US008859972B2

(12) United States Patent
Cummings et al.

(10) Patent No.: US 8,859,972 B2
(45) Date of Patent: Oct. 14, 2014

(54) INFRA-RED REFLECTIVE OCCLUSION SENSORS

(75) Inventors: David Charles Cummings, Richardson, TX (US); Andrew Peter Nelson, Dallas, TX (US); Russell Paul Meyer, Plano, TX (US)

(73) Assignee: Nestec S.A., Vevey (CH)

( * ) Notice: Subject to any disclaimer, the term of this patent is extended or adjusted under 35 U.S.C. 154(b) by 46 days.

(21) Appl. No.: 13/391,345

(22) PCT Filed: Jul. 8, 2010

(86) PCT No.: PCT/US2010/041320
§ 371 (c)(1),
(2), (4) Date: Apr. 30, 2012

(87) PCT Pub. No.: WO2011/025588
PCT Pub. Date: Mar. 3, 2011

(65) Prior Publication Data
US 2012/0280130 A1 Nov. 8, 2012

Related U.S. Application Data

(60) Provisional application No. 61/237,711, filed on Aug. 28, 2009, provisional application No. 61/236,899, filed on Aug. 26, 2009.

(51) Int. Cl.
*G01J 5/02* (2006.01)
*A61M 5/168* (2006.01)
(52) U.S. Cl.
CPC ... *A61M 5/16831* (2013.01); *A61M 2205/3306* (2013.01)
USPC .......................................................... 250/353

(58) Field of Classification Search
CPC .......................................................... G01J 5/08
USPC .......................................................... 250/353
See application file for complete search history.

(56) References Cited

U.S. PATENT DOCUMENTS 4,277,226 A * 7/1981 Archibald ........................ 417/38
5,237,858 A * 8/1993 Ohsaki et al. ................. 73/61.72
(Continued)

FOREIGN PATENT DOCUMENTS

GB 1532685 A * 11/1978
WO 98/04301 2/1998
WO 2007/141786 12/2007

OTHER PUBLICATIONS

International Search Report PCT/US2010/041320 dated Oct. 28, 2010—3 pages.

(Continued)

*Primary Examiner* — Kiho Kim
(74) *Attorney, Agent, or Firm* — K&L Gates LLP

(57) ABSTRACT

Occlusion sensor systems and methods of using the occlusion sensor systems are provided. In a general embodiment, the present disclosure provides a sensor device includes a tube and an infra-red reflective sensor comprising an infra-red light emitter and an infra-red phototransistor receiver or photo-diode. The infra-red reflective sensor and the infra-red phototransistor receiver or photo-diode are positioned at or near the tube so that an infra-red light can be transmitted to a portion of the tube and at least a portion of the infra-red light reflected off the portion of the tube can be detected by the infra-red phototransistor receiver or photo-diode.

17 Claims, 4 Drawing Sheets

(56) References Cited

U.S. PATENT DOCUMENTS

| | | | |
|---|---|---|---|
| 5,777,221 A * | 7/1998 | Murthy et al. | 73/149 |
| D455,489 S | 4/2002 | Beck et al. | |
| 6,659,976 B2 | 12/2003 | Beck et al. | |
| D501,924 S | 2/2005 | Cise et al. | |
| D504,506 S | 4/2005 | Beck et al. | |
| D505,199 S | 5/2005 | Beck et al. | |
| D507,647 S | 7/2005 | Beck et al. | |
| 8,242,920 B1 * | 8/2012 | Mostowfi et al. | 340/605 |
| 2002/0084415 A1 * | 7/2002 | Kawano et al. | 250/339.09 |
| 2005/0063847 A1 * | 3/2005 | Fathallah et al. | 417/477.2 |
| 2007/0151346 A1 | 7/2007 | Malmstrom et al. | |
| 2008/0199623 A1 * | 8/2008 | Terry | 427/402 |
| 2008/0294094 A1 | 11/2008 | Mhatre et al. | |
| 2009/0093786 A1 * | 4/2009 | Renaux et al. | 604/500 |
| 2009/0118667 A1 | 5/2009 | Haueter et al. | |
| 2010/0082011 A1 * | 4/2010 | Lewis et al. | 604/503 |

OTHER PUBLICATIONS

Written Opinion of the International Searching Authority PCT/US2010/041320 dated Oct. 28, 2010—6 pages.

* cited by examiner

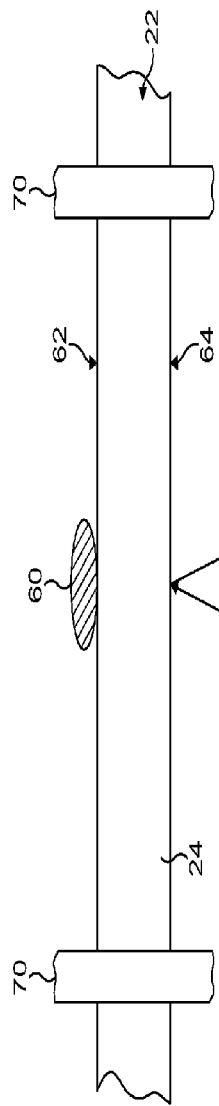
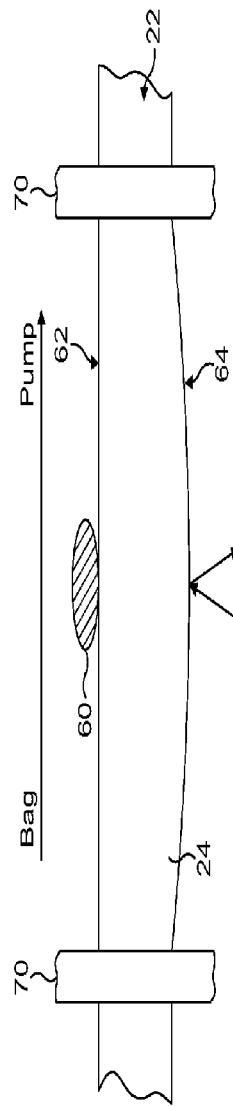
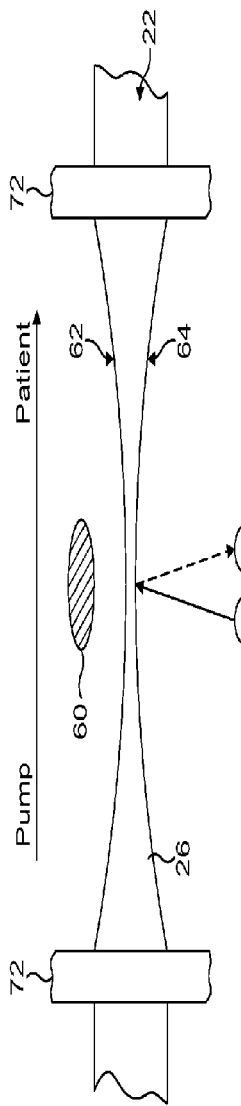

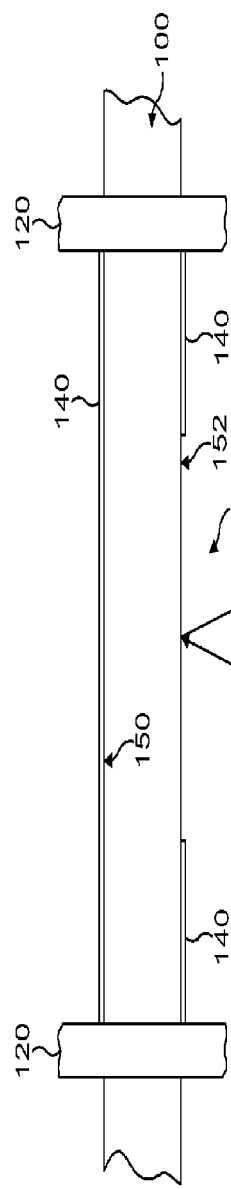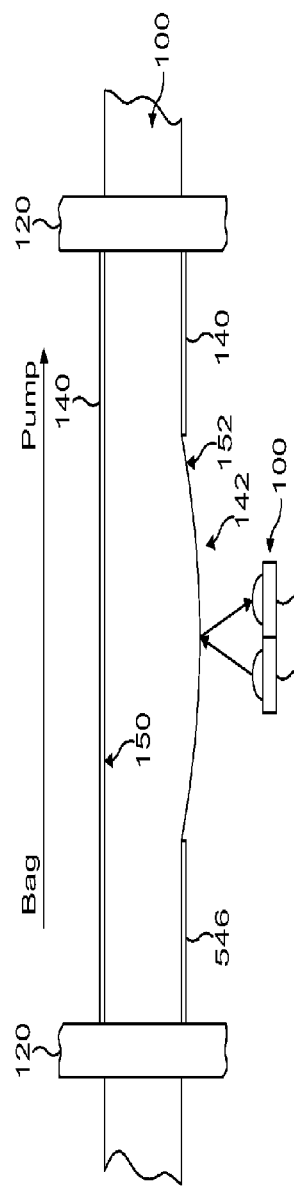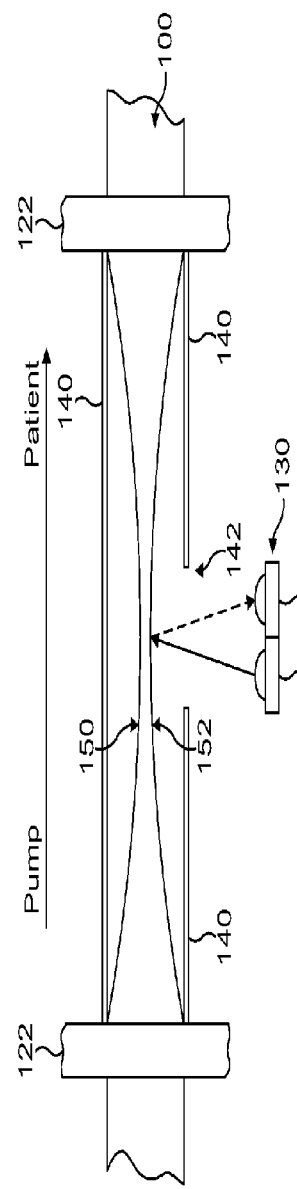

INFRA-RED REFLECTIVE OCCLUSION SENSORS

CROSS REFERENCE TO RELATED APPLICATIONS

The present application is a National Stage of International Application No. PCT/US2010/041320, filed on Jul. 8, 2010, which claims priority to U.S. Provisional Patent Application No. 61/236,899, filed on Aug. 26, 2009, and U.S. Provisional Patent Application No. 61/237,711, filed on Aug. 28, 2009, the entire contents of which are being incorporated herein by reference.

BACKGROUND

The present disclosure generally relates to health and nutrition. More specifically, the present disclosure relates to devices and methods for detecting occlusions in the tubing set of fluid pump systems.

The delivery of nutritional compositions to mammals, such as human patients, that cannot orally ingest food or other forms of nutrition is often of critical importance. For example, enteral bottles and containers having feeding tubes that deposit food directly into the gastrointestinal tract at a point below the mouth are often used to sustain life while a patient is unable, or refuses, to take food orally. Bottles and containers, feeding tubes and other artificial delivery systems and routes can be used temporarily during the treatment of acute medical conditions. For chronic medical conditions, such systems and routes can be used as part of a treatment regimen that lasts for the remainder of a patient's life. No matter the duration of use, these devices often provide the only means for feeding the patient.

The use of enteral feeding pumps, in conjunction with an enteral feeding tube set as part of an enteral feeding system, for the administering of medical fluids is also well known in the medical arts. The enteral feeding tube set will typically include several long sections of tubing, connected to a centralized, shorter section of tubing that can be incorporated into a pumping device. One common concern with the enteral feeding tube set is that it may become blocked or occluded over time without the patient's knowledge. If the feeding tube set does become occluded, the enteral feeding system may malfunction, and the patient will not receive the necessary nutrition, which could lead to adverse health problems for the patient.

SUMMARY

The present disclosure relates to occlusion sensor systems and methods of using the occlusion sensor systems. In a general embodiment, the present disclosure provides a sensor device including a tube and an infra-red reflective sensor including an infra-red light emitter and an infra-red phototransistor receiver and/or photo-diode. The infra-red reflective sensor is positioned so that an infra-red light can be transmitted to a portion of the tube and at least a portion of the infra-red light reflected off the portion of the tube can be detected by the infra-red phototransistor receiver or photo-diode. The infra-red light emitter can be a light emitting diode.

In an embodiment, any suitable portion of the tube includes opaque walls. In another embodiment, at least a portion of the tube includes an infra-red reflective surface. The tube can be contained within a tube housing that defines an opening or window for the infra-red light to reach the tube.

In another embodiment, the present disclosure provides an occlusion sensor system including a cassette removably attachable to a pumping device with the cassette including a tube and one or more infra-red reflective sensors including an infra-red light emitting diode and an infra-red phototransistor receiver or photo-diode. The infra-red reflective sensor is positioned so that an infra-red light can be transmitted to the tube and detected by the infra-red phototransistor receiver or photo-diode.

In an embodiment, the cassette includes one or more bias bumps adjacent to a portion of the tube. In an embodiment, the pumping device is an enteral feeding pump, and the tube can be part of an enteral feeding tube set.

In an alternative embodiment, the present disclosure provides an occlusion sensor system including an enteral feeding pump having one or more infra-red reflective sensors. The infra-red reflective sensor can include an infra-red light emitting diode and an infra-red phototransistor receiver or photo-diode. The occlusion sensor system further includes a cassette removably attached to the enteral feeding pump and a tube attached to the removable cassette. The infra-red reflective sensor is positioned so that an infra-red light can be transmitted to a portion of the tube and detected by the infra-red phototransistor receiver or photo-diode. The infra-red reflective light emitting diode and the infra-red phototransistor receiver or photo-diode can be positioned on the same side within the enteral feeding pump. The tube can be part of an enteral feeding tube set.

In yet another embodiment, the present disclosure provides a method of detecting occlusions in a tubing set for an enteral feeding system. The method comprises detecting an occlusion within an enteral feeding tube that is part of the tubing set by transmitting an infra-red light to the feeding tube and detecting an amount of reflected infra-red light using the infra-red phototransistor receiver or photo-diode based on an expanding or contracting of the feeding tube. The feeding tube can be incorporated as part of a cassette that can be attached to a pumping device. In an embodiment, an enteral feeding cycle is stopped if an occlusion is detected in the tube.

An advantage of the present disclosure is to provide an improved in-line sensor for detecting occlusions in a tubing set.

Another advantage of the present disclosure is to provide an improved method for detecting occlusions in a tubing set for enteral feeding.

Yet another advantage of the present disclosure is to provide an improved sensor for detecting occlusions that is cost-effective.

Still another advantage of the present disclosure is to provide an improved sensor for detecting occlusions that is simple to operate.

Additional features and advantages are described herein, and will be apparent from the following Detailed Description and the figures.

BRIEF DESCRIPTION OF THE FIGURES

FIGS. 3A-3C show the detection of an occlusion in a tube in an embodiment of the present disclosure.

FIGS. 4A-4C show the detection of an occlusion in a tube contained within a tube housing in another embodiment of the present disclosure.

DETAILED DESCRIPTION

The present disclosure relates to occlusion sensor systems and methods of using the occlusion sensor systems. The occlusion sensor systems utilize infra-red technology and can be incorporated in pumping devices. The pumping device can be part of an enteral administration device or system that administers nutritional compositions to a person or patient in need of same.

As used herein, the term "nutritional composition" includes, but is not limited to, complete nutritional compositions, partial or incomplete nutritional compositions, and disease or condition specific nutritional compositions. A complete nutritional composition (i.e. those which contain all the essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as nutritional supplements.

A disease or condition specific nutritional composition is a composition that delivers nutrients or pharmaceuticals and can be a complete or partial nutritional composition. Disease or condition specific nutritional compositions are those designed to aid with a given situation, such as Impact® sold by Nestlé Nutrition to decrease post-operative infections, Diabetisource AC® sold by Nestlé Nutrition for people with diabetes or hyperglycemia, and Novasource® Pulmonary sold by Nestlé Nutrition for those patients with pulmonary disease or those requiring ventilator support.

Figure 1:
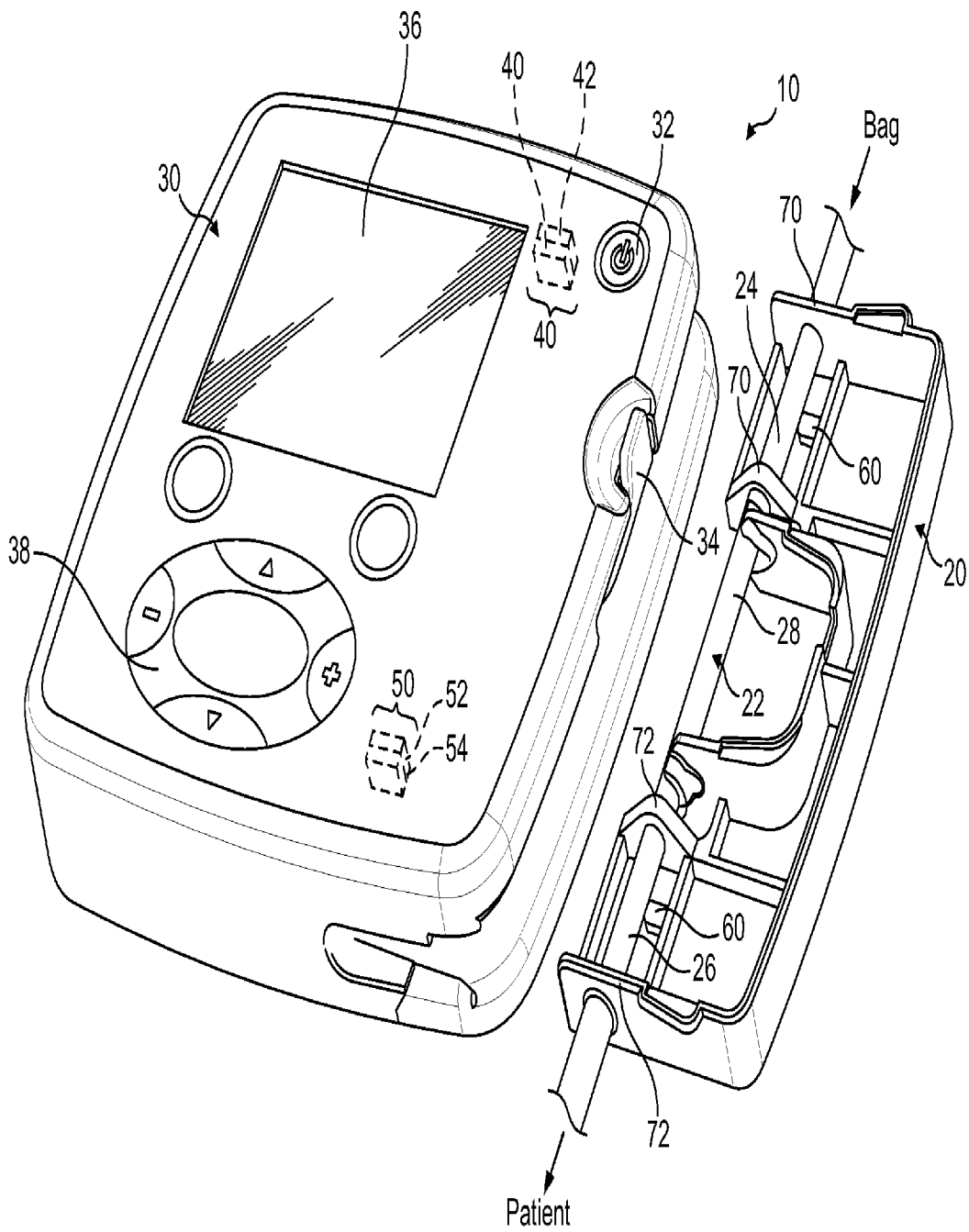
FIG. 1 shows a pumping device and cassette having an occlusion sensor system in an embodiment of the present disclosure.
Figure 2:
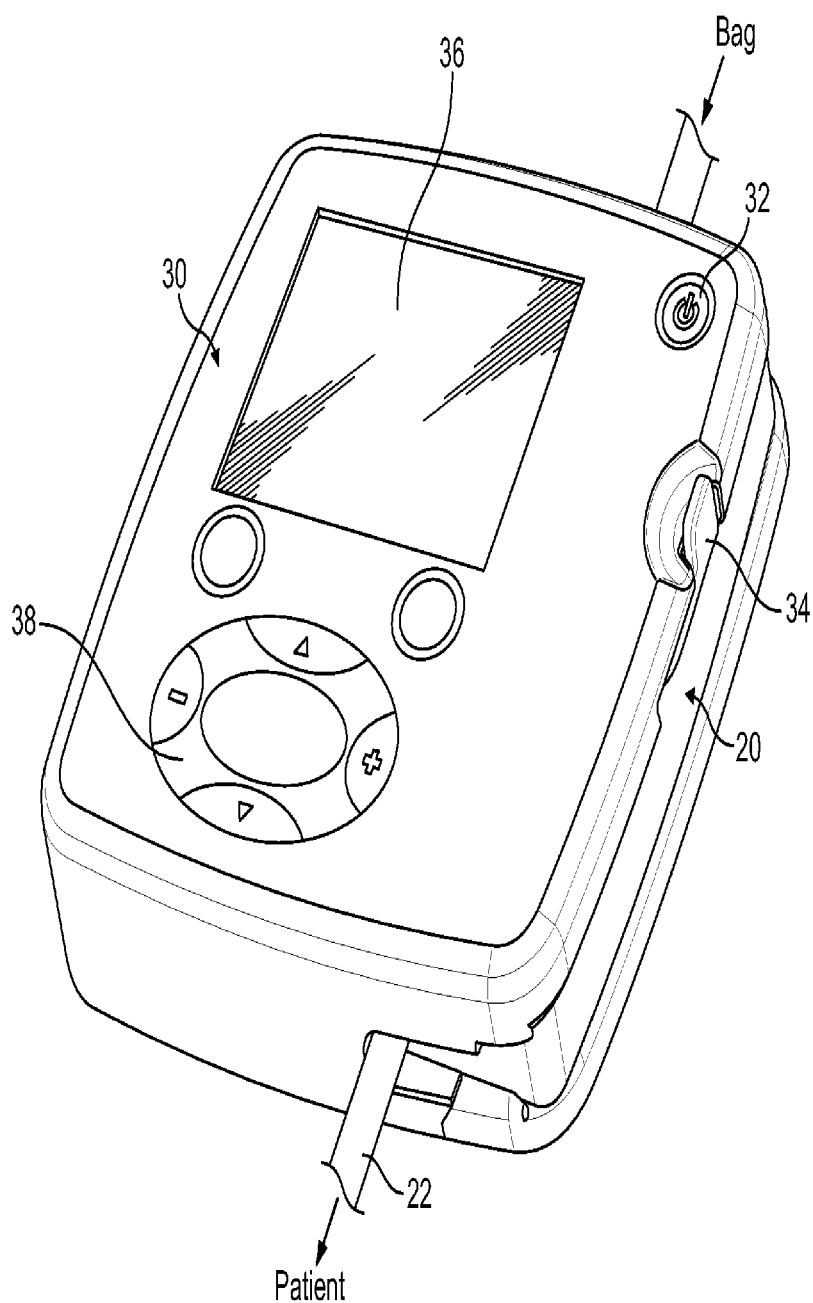
FIG. 2 shows the pumping device and the cassette of FIG. 1 with the cassette inserted into the pumping device.

As illustrated in FIGS. 1-2, in an embodiment, the present disclosure provides an occlusion sensor system 10 including a cassette 20 removably attachable to a pumping device 30. Pumping device 30 can include one or more infra-red sensors 40 and 50. Infra-red sensors 40 and 50 include infra-red reflective light emitters 42 and 52, respectively. Infra-red sensor 40 and 50 further include infra-red phototransistor receiver or photo-diodes 44 and 54, respectively, positioned as part of the occlusion sensor system 10 within an inner section of pumping device 30. Infra-red light emitters 42 and 52 can be a light emitting diode.

Infra-red sensors 40 and 50 can be any suitable infra-red sensor having an infra-red emitting device and a detection device. Non-limiting examples of infra-red sensors 40 and 50 include infra-red sensors developed under the QRD series by Fairchild Semiconductor. Infra-red light emitters 42 and 52 and infra-red phototransistor receiver or photo-diodes 44 and 54 can be supported or positioned on any suitable support (e.g. within pumping device 30).

Cassette 20 further includes tube 22 as part of the occlusion sensor system. When cassette 20 is inserted into pumping device 30, infra-red reflective light emitters 42 and 52 and infra-red phototransistor receiver or photo-diodes 44 and 54 can be positioned to lay side-by-side and along the length of tube 22 at different portions 24 and 26, respectively, of tube 22 as illustrated in FIG. 1.

Fluid can flow through tube 22 in the direction from first portion 24 to second portion 26. Tube 22 can extend from portion 24 to be connected to bag containing a nutritional composition source and can extend from portion 26 to be connected to the person receiving the nutrition composition.

Infra-red sensors 40 and 50 can be positioned on either side of a pump (not shown) within pumping device 30. For example, the pump can be located at a central location of pumping device 30 and would interact with a portion 28 of tube 22 located on cassette 20. Accordingly, infra-red sensor 40 interacts with portion 24 of tube 22 located upstream of the pump (e.g., receive a nutritional composition from a container or bag). Infra-red sensor 50 would interact with portion 26 of tube 22 located downstream of the pump (e.g., sending a nutritional composition to the patient).

Pumping device 30 can be an enteral feeding pump. The pump contained within pumping device 30 can be a peristaltic pump. Non-limiting examples of pumping devices are described in U.S. Pat. No. 6,659,976, which is incorporated herein by reference. Pumping device 30 can include a monitor/information screen 36 and a control pad 38 for operating pumping device 30. Monitor/information screen 36 and control pad 38 can also be used in conjunction with the occlusion sensor system in embodiments of the present disclosure. Pumping device 30 can further include a power button 32 and a release mechanism 34 for releasing cassette 20 from pumping device 30.

Cassette 20 can include a housing or support structure having any suitable shape such as the one shown in FIG. 1. Cassette 20 can be design to be inserted partially or wholly within pumping device 30 as seen in FIG. 2. The design of cassette 20 can help in loading an enteral feeding tube set into pumping device 30 without having to route/guide the tubes or stretch the tubes from the tube set over a rotor (e.g. part of a peristaltic pump) contained within pumping device 30. Non-limiting examples of alternative cassette configurations are described in U.S. Pat. Nos. D504,506, D505,199, D455,489, D501,924 and D507,647, which are incorporated herein by reference. Cassette 20 can be made from any suitable rigid, semi-rigid or flexible material. Cassette 20 can also have a dark pigment added to its material. Cassette 20 can also have a carbon black pigment added to its material. Cassette 20 can also have a dark pigment added to its material to absorb light. Cassette 20 can also have a carbon black pigment added to its material to absorb light. Cassette 20 can also have a dark pigment added to its material to absorb ambient light. Cassette 20 can also have a carbon black pigment added to its material to absorb ambient light. Cassette 20 can also be designed such that it can be inserted into pumping device 30 only one way.

Tube 22 can be flexible and have portions that are rigid or semi-rigid. Tube 22 can be a feeding tube and be constructed and arranged to be incorporated with the rotors of a pump (e.g. peristaltic pump) in pumping device 30.

During operation as shown in FIGS. 3A-3C, a pump (not shown) within pumping device 30 located near portion 28 pumps the nutritional composition from a bag through cassette 20 via tube 22 to a patient. If there is no occlusion either between the bag and the pump or the pump and the patient, the sidewalls of tube 22 at portions 24 and 26 remain stationary (e.g., do not expand or contract). Portions 70 and 72 of the cassette 20 covering tube 22 on either side of portions 24 and 26, respectively, act as tube retention mechanisms that help retain tube 22 in position within cassette 20.

If an occlusion in tube 22 occurs upstream of the pump (e.g., between the bag and the pump), the pump will continue to attempt to pass the nutritional composition through tube 22. However, because no nutritional composition is passing through, the sidewalls 62 and 64 of portion 24 of tube 22 will begin to contract (e.g., move inward) as shown in FIG. 3B. At the same time, infra-red light emitter 42 will emit infra-red light toward sidewall 64 of tube 22 facing infra-red light emitter 42. Because sidewall 64 will be opaque or include an infra-red reflective material, sidewall 64 will reflect the infra-red light back to be detected by infra-red phototransistor receiver or photo-diode 44.

An intensity or amount of the reflected infra-red light will be proportional to the distance that sidewall 64 is from infra-red sensor 40. As a result, if the intensity of the reflected light changes because sidewall 64 is further away from infra-red sensor 40, this shows that sidewall 64 has contracted thereby signifying that the occlusion has occurred upstream of the pump. The intensity of the detected infra-red emitted light at various stages of contraction of sidewall 64 can be measured and calibrated so that the amount of contraction (e.g., related to the strength of the occlusion) can be determined using a computer processor, for example, on pumping device 30. It is understood that the change direction is dependant upon the position of the tubing in relation to optimal focal point (maxima for photo detector current) of the sensor. If the initial spacing is less than the maxima point, then as the tubing shrinks the received reflected energy will increase. The inverse occurs if we start with the tubing past the maxima point, the reflected energy will in that case decrease as the tubing contracts. Either mode can be useful but the selection can be a function of the mechanical constraints imposed in integrating the sensor as part of the larger system.

If an occlusion in tube 22 occurs downstream of the pump (e.g., between the pump and the patient), the pump will continue to attempt to pass the nutritional composition through tube 22. However, because the accumulating nutritional composition is building pressure up in tube 22 by passing through, the sidewalls 62 and 64 of portion 26 of tube 22 will begin to expand or bulge (e.g., move outward). At the same time, infra-red light emitter 52 will emit infra-red light toward sidewall 64 of tube 22 facing infra-red light emitter 52.

An intensity or amount of the reflected infra-red light will be proportional to the distance that sidewall 64 is from infra-red sensor 50. As a result, if the intensity of the reflected light changes because sidewall 64 is closer to infra-red sensor 50, this shows that sidewall 64 has expanded thereby signifying that the occlusion has occurred downstream of the pump. The intensity of the detected infra-red emitted light at various stages of sidewall 64 can be measured and calibrated so that the amount of expansion (e.g., related to the strength of the occlusion) can be determined using a computer processor, for example, on pumping device 30.

As illustrated in FIGS. 1 and 3A-3C, cassette 20 can include a bias bump 60 that is adjacent to tube 22 at portions 24 and 26. Bias bump 60 can be used to prevent sidewall 62 of tube 22 located on the same side as bias bump 60 from expanding past bias bump 60. As a result, sidewall 64 of tube 22 opposite bias bump 60 can expand further toward infra-red sensors 40 and 50 than would be possible without bias bump 60. This can increase the sensitivity of the occlusion detection.

In another embodiment shown in FIGS. 4A-4C, a tube 100 can be positioned with a tube housing 140 that is integrated with a portion 120 of a cassette that holds tube 100. Tube housing 140 further defines a window 142. Tube housing 140 can be made, for example, from a molded, plastic chamber constructed and arranged to hold tube 100. For example, tube housing 140 can be made from an opaque polyvinyl chloride material. Any portion of tube housing 140 can include an infra-red transparent surface or a solid surface to prevent transmission of infra-red light or absorb infra-red light so that infra-red light only passes though window 142.

During operation as shown in FIGS. 4A-4C, a pump (not shown) pumps the nutritional composition from a bag through tube 100 to a patient. If there is no occlusion either between the bag and the pump or the pump and the patient, the sidewalls of tube 100 remain stationary (e.g., do not expand or contract). The portions 120 and 122 of the cassette covering tube 100 act as tube retention mechanisms that retain tube 100 in position with the cassette.

If an occlusion in tube 100 occurs upstream of the pump (e.g., between the bag and the pump), the pump will continue to attempt to pass the nutritional composition through tube 100. However, because no nutritional composition is passing through, the sidewalls 150 and 152 of tube 100 located upstream of the pump will begin to contract (e.g., move inward) as shown in FIG. 4B. At the same time, infra-red light emitter 112 will emit infra-red light toward sidewall 152 of tube 100 through window 142 of tube housing 140. Because sidewall 152 will be opaque or include an infra-red reflective material, sidewall 152 will reflect the infra-red light back to be detected by an infra-red phototransistor receiver or photo-diode 114 of an infra-red sensor system 110. The intensity or amount of the reflected infra-red light is proportional to the distance that sidewall 152 is from infra-red sensor 110, and the change in intensity signifies that the occlusion has occurred upstream of the pump.

If an occlusion in tube 100 occurs downstream of the pump (e.g., between the pump and the patient), the pump will continue to attempt to pass the nutritional composition through tube 100. However, because the accumulating nutritional composition is building pressure up in tube 100 by passing through, the sidewalls 150 and 152 of tube 100 downstream of the pump will begin to expand or bulge (e.g., move outward) as shown in FIG. 4C. At the same time, infra-red light emitter 132 of infra-red sensor 130 will emit infra-red light toward sidewall 152 of tube 100. The change in intensity of the reflected light increases measured by infra-red phototransistor receiver or photo-diode 134 shows that sidewall 152 has expanded thereby signifying that the occlusion has occurred downstream of the pump. Because of tube housing 140, only a portion of tube 100 located at window 142 will expand or pass through window 142 thereby providing a more concise expansion of tube 100.

Infra-red sensors 110 and 130 can be positioned in a suitable manner with respect to window 142 of tube housing 140 and with respect to each other so that a desired amount of the infra-red light sent out by infra-red sensors 110 and 130 and reflected off of tube 100 is detected by infra-red sensors 110 and 130. Infra-red light emitters 112 and 132 and infra-red phototransistor receiver or photo-diodes 114 and 134, respectively, can be placed side-by-side in contact with each other or spaced apart.

In an alternative embodiment, the present disclosure provides a cassette that incorporates an infra-red reflective sensor including an infra-red light emitter and an infra-red phototransistor receiver or photo-diode. In this regard, the pumping device does not house the infra-red reflective sensor. However, the infra-red reflective sensor on the cassette can be constructed and arranged to interact with the pumping device so that the results of the infra-red reflective sensor can be displayed on a monitor of the pumping device.

In yet another embodiment, the present disclosure provides a method of detecting occlusions in a tubing for an enteral feeding system. The method comprises providing an occlusion sensing system including a feeding tube and an infra-red reflective sensor including an infra-red light emitting diode and an infra-red phototransistor receiver or photo-diode. The feeding tube can be incorporated as part of a cassette that can be attached to a pumping device of the enteral feeding system.

The method further comprises detecting an occlusion within the feeding tube by transmitting an infra-red light toward the feeding tube and detecting reflected infra-red light using the infra-red phototransistor receiver or photo-diode, for example, based on an amount of the expanding or contracting of the feeding tube. If occlusions are detected in the feeding tube, the pumping device can be stopped, for example, during an enteral feeding cycle.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An occlusion sensor system comprising:
 a pumping device;
 a cassette removably attachable to the pumping device, the cassette comprising a tube;
 an infra-red reflective sensor comprising an infra-red light emitting diode and an infra-red phototransistor receiver or photo-diode, being positioned to lay side-by-side, the infra-red reflective sensor being positioned so that an infra-red light can be directly transmitted to a respective portion of the tube comprising an infra-red reflective surface and at least a portion of the infra-red light reflected off the portion of the tube can be detected by the infra-red phototransistor receiver or photo-diode; and
 a processor configured to determine a presence of an occlusion based on the infra-red reflective sensor and to stop pumping in response to the occlusion, and the processor is programmed to use the intensity of the detected infra-red light at various stages of contraction of the sidewall of the portion of the tube to determine an amount of contraction or expansion that is used to determine a strength of the occlusion.

2. The occlusion sensory system of claim 1, wherein the cassette comprises a bias bump adjacent to a portion of the tube.

3. The occlusion sensor system of claim 1, wherein the tube comprises opaque walls.

4. The occlusion sensor system of claim 1, wherein the pumping device is an enteral feeding pump.

5. The occlusion sensor system of claim 1, wherein the tube is part of an enteral feeding tube set.

6. The occlusion sensor system of claim 1, wherein the tube is contained within a tube housing that defines a window.

7. The occlusion sensor system of claim 1, wherein the at least one infra-red reflective sensor is comprised in said pumping device.

8. The occlusion sensor system of claim 1, wherein the infra-red light emitting diode and infra-red phototransistor receiver or photo-diode are in contact with each other.

9. The occlusion sensor system of claim 1, wherein the infra-red reflective surface is positioned on the exterior of the portion to which the infra-red light is directly transmitted.

10. A method of using an occlusion sensor in a tubing set for an enteral feeding system comprising an occlusion sensor system comprising a pumping device, a cassette removably attachable to the pumping device, the cassette comprising an enteral feeding tube, and an infra-red reflective sensor comprising an infra-red light emitting diode and an infra-red phototransistor receiver or photo-diode being positioned to lay side-by-side, the method comprising:
 detecting an occlusion within the enteral feeding tube by directly transmitting an infra-red light via the infra-red light emitting diode to a respective portion of the feeding tube comprising an infra-red reflective surface and detecting an amount of reflected infra-red light being reflected off the portion of the feeding tube using the infra-red phototransistor receiver or photo-diode based on an expansion or contraction of the feeding tube, and the detecting of an occlusion comprises determining the distance from the infra-red reflective sensor to the portion of the feeding tube using the amount of infra-red light reflected off the portion of the feeding tube; and
 stopping an enteral feeding cycle if an occlusion is detected in the feeding tube based on the reflected infra-red light.

11. The method of claim 10, wherein the infra-red reflective surface is positioned on the exterior of the portion to which the infra-red light is directly transmitted.

12. The method of claim 11, wherein the feeding tube is incorporated as part of a cassette that can be attached to a pumping device.

13. The method of claim 12, wherein the cassette is removably attachable to the pumping device.

14. The method of claim 12, wherein the cassette comprises a bias bump adjacent to a portion of the tube.

15. The method of claim 12, wherein the pumping device is an enteral feeding pump.

16. The method of claim 11, wherein the tube comprises opaque walls.

17. The method of claim 11, wherein the tube is contained within a tube housing that defines a window.

* * * * *